United States Patent [19]

Goodman

[11] Patent Number: 4,557,255

[45] Date of Patent: Dec. 10, 1985

[54] URETEROSCOPE

[76] Inventor: Tobias M. Goodman, Passpataug Rd., Weekapaug, R.I. 02891

[21] Appl. No.: 525,620

[22] Filed: Aug. 22, 1983

[51] Int. Cl.⁴ ............................................. A61B 1/30
[52] U.S. Cl. ........................................ 128/7; 128/328; 128/344; 128/345
[58] Field of Search ................... 124/7, 328, 4, 5, 344, 124/345, 303.15, 343, 341, 6

[56] References Cited

U.S. PATENT DOCUMENTS

| | | | |
|---|---|---|---|
| 1,003,232 | 9/1911 | Cerbo | 128/7 |
| 1,662,227 | 3/1928 | Allyn | 128/7 |
| 2,469,906 | 5/1949 | Wallace | 128/7 |
| 3,472,230 | 10/1969 | Fogarty | 128/328 |
| 4,027,674 | 6/1977 | Tessler et al. | 128/328 |

FOREIGN PATENT DOCUMENTS

| | | | |
|---|---|---|---|
| 2057636 | 3/1972 | Fed. Rep. of Germany | 128/328 |
| 490469 | 2/1976 | U.S.S.R. | 128/344 |

OTHER PUBLICATIONS

American Cystoscope Makers Incorporated Pamphlet, pp. 73, 74 and 77–84, 1241 Lafayette Ave., N.Y. 59, N.Y.

Primary Examiner—Michael H. Thaler
Attorney, Agent, or Firm—Salter & Michaelson

[57] ABSTRACT

A ureteroscope for carrying out surgical procedures in the lower ureter area under direct visual control. The ureteroscope includes a sheath having a main portion which is dimensioned to be received in the urethra so that it extends into the urinary bladder, a tapered portion which extends from the main portion and a terminal portion which is dimensioned to be received in the ureter. The ureteroscope also includes a telescope assembly which extends through the sheath and is operable for viewing the area of the ureter adjacent the distal end of the sheath. Remotely operable jaws are provided in one embodiment of the device for retrieving stones and the like, and another embodiment is constructed for use in combination with a variety of appliances for carrying out various surgical procedures in the ureter.

16 Claims, 16 Drawing Figures

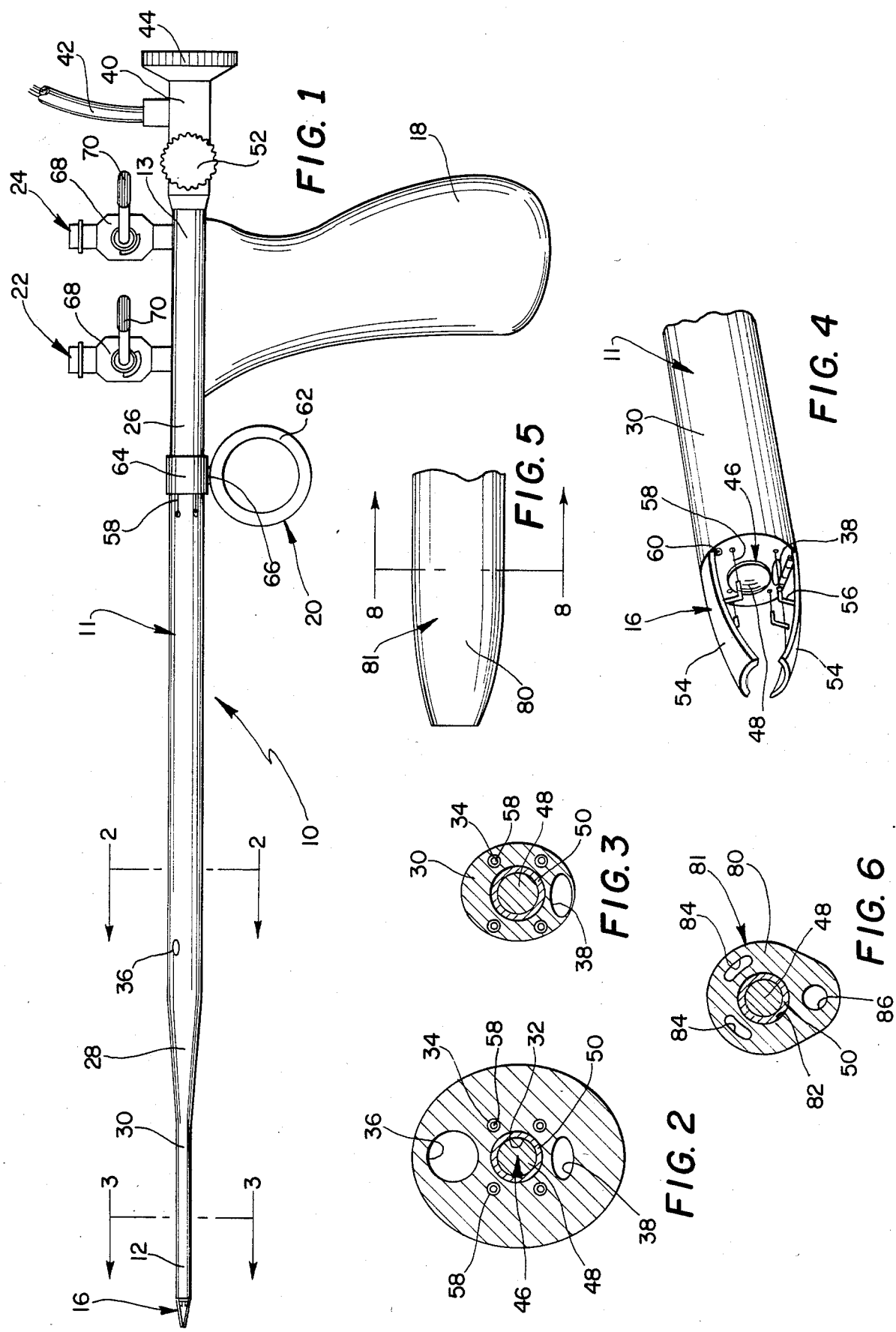

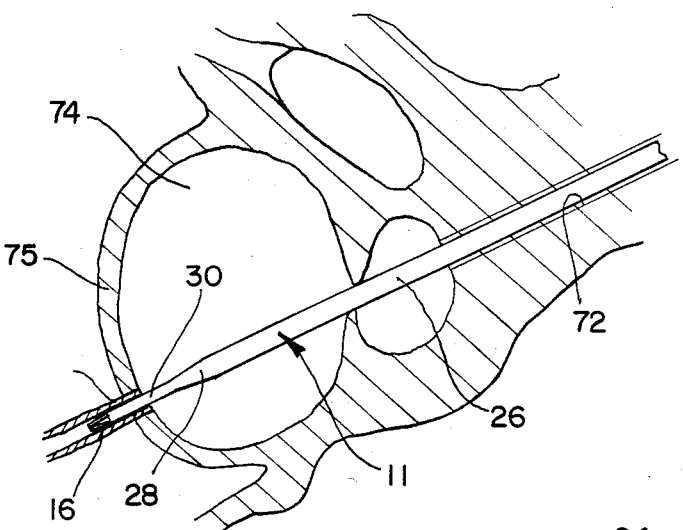
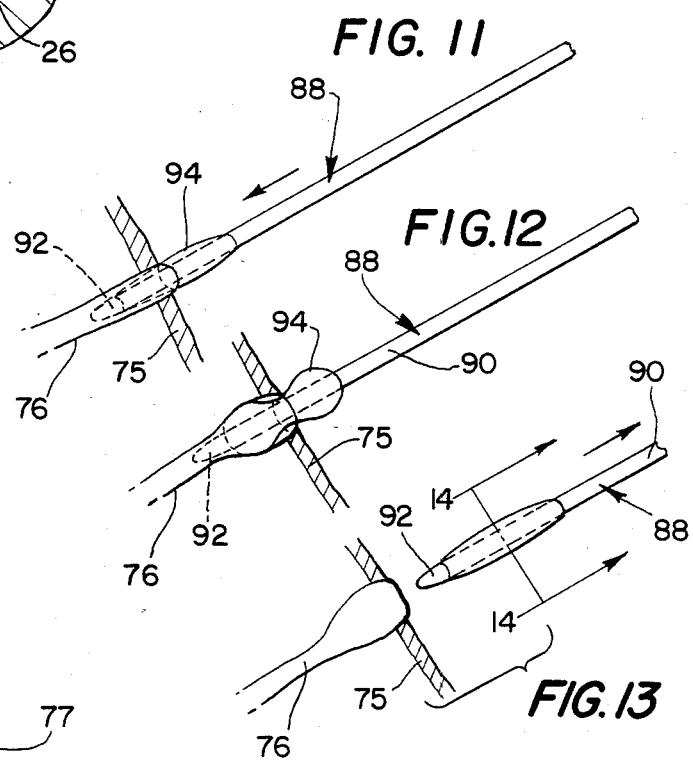
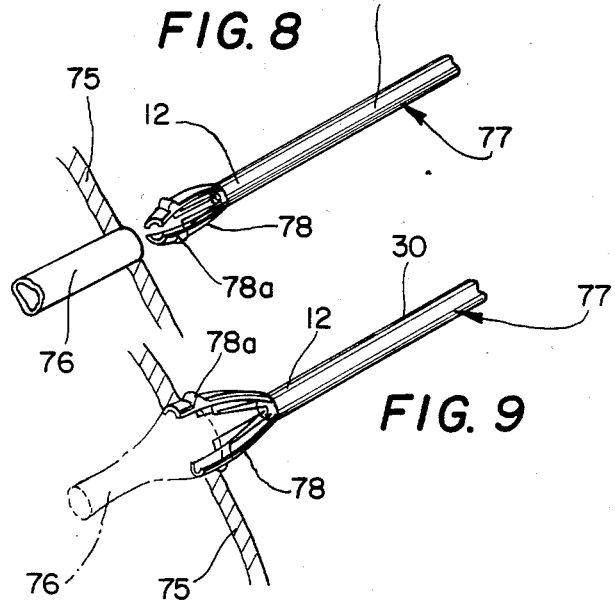

URETEROSCOPE

BACKGROUND AND SUMMARY OF THE INVENTION

The instant invention relates to a urological endoscopic device for the human body and more particularly to a ureteroscope for the operative management of the disease processes in the lower ureter under direct visual control.

It has been found that a variety of disease processes affect the lower ureter, particularly the last several centimeters of the ureter, in the area where it enters the urinary bladder. These disease processes include stones, tumors, and strictures and have heretofore been primarily treated with blind surgical devices which rely on X-ray and/or tactile control or with open surgery. While a number of urological endoscopic devices have heretofore been available, they have not been operative for providing direct visual control within the ureter, and hence they have not been entirely effective for treating disease processes within the ureter. Specifically, while the known endoscopic devices have included appliances which are adapted for operation within the ureter, they have not been operable for carrying out surgical procedures in the ureter under direct visual control. Common complications resulting from the use of such blind devices are uretal tear or rupture, as well as injury resulting from inadvertently impacted devices which in many instances has required surgery.

The instant invention provides a novel endoscopic device which is operable for carrying out procedures within the ureter under direct visual control. In this regard, the ureteroscope of the instant invention comprises a substantially straight, substantially rigid elongated sheath having distal and proximal ends, the sheath comprising an elongated main portion which is dimensioned for insertion into a patient so that it extends through the urethra and substantially through the bladder of the patient, a tapered portion which extends from the end of the main portion, and a reduced terminal portion which extends from the tapered portion and is dimensioned to be received in the ureter of a patient. A longitudinal telescope passage is provided extending through the sheath, and the ureteroscope further comprises a telescope assembly which is received in the passage to provide visual communication between the distal and proximal ends of the instrument. Accordingly, when the instrument is inserted into a patient so that the terminal portion of the instrument is received in the ureter of the patient, direct viewing of the ureter in the area thereof adjacent the distal end of the instrument is possible from the proximal end of the instrument through the telescope assembly. In the preferred embodiment of the instrument, irrigation passages are provided in the sheath for irrigating both the bladder and ureter areas of the patient. In one embodiment of the instrument, jaws are provided on the distal end of the sheath and are operable for carrying out various specific surgical functions within the ureter under direct visual control. In another embodiment of the instrument, a longitudinal appliance passage is provided in the sheath for receiving various appliances which are adapted for carrying out specific operative procedures within the ureter. One such appliance comprises a net assembly which functions in a purse-like manner for retrieving stones and the like from within the ureter. Another appliance comprises a dilating balloon assembly which includes a balloon which is inflatable to a barbell-like configuration so that it is operable for dilating the area of the ureter where it passes through the bladder wall. Specifically, the barbell-like balloon is positionable in a ureter so that opposite ends of the balloon are on opposite sides of the bladder wall. Thereafter the balloon can be inflated with the bladder wall positioned at the central portion of the barbell-like balloon so that the balloon does not tend to slip out of position and remains properly oriented in the ureter. Accordingly, it is seen that the ureteroscopic instrument of the instant invention is operable, in its various embodiments, for carrying out a variety of surgical procedures in the ureter under continuous direct visual control whereby the likelihood of success of a given procedure is maximized, and whereby complications and injury to the patient are minimized.

It is, therefore, a primary object of the instant invention to provide a ureteroscopic instrument which is operable for carrying out surgical procedures within the ureter under direct visual control.

Another object of the instant invention is to provide a purse-like surgical net which is operable for retrieving stones and the like from within the human body.

Another object of the instant invention is to provide an effective means for dilating the human ureter.

A still further object of the instant invention is to provide a urological endoscopic device which is operable for carrying out operative procedures within the ureter under direct visual control and which includes means for irrigating both the bladder and the ureter.

An even further object of the instant invention is to provide a urological endoscopic device whereby operative procedures can be carried out in the ureter with a relatively high likelihood of success and with minimal risk to a patient.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention:

FIG. 1 is a side elevational view of a first embodiment of the ureteroscope of the instant invention;

FIG. 2 is a sectional view taken along line 2—2 in FIG. 1;

FIG. 3 is a sectional view taken along line 3—3 in FIG. 1;

FIG. 4 is an enlarged perspective view of the distal end portion of the ureteroscope of the instant invention;

FIG. 5 is an enlarged side elevational view of the distal end portion of a second embodiment of the ureteroscope;

FIG. 6 is a sectional view taken along line 6—6 in FIG. 5;

FIG. 7 is a sectional view of the uretha, bladder, and ureter area of a human body with the ureteroscope of the instant invention received therein;

FIGS. 8 and 9 are enlarged perspective views illustrating the operation of the ureteroscope as embodied with jaws in the dilation of a ureter;

FIG. 10 is a perspective view of the distal end of the ureteroscope with a stone received in the jaws;

FIGS. 11 through 13 illustrate the dilation of a ureter with the barbell-like balloon appliance of the ureteroscope;

FIG. 14 is a sectional view taken along line 14—14 in FIG. 13;

DESCRIPTION OF THE INVENTION

Figure 15:
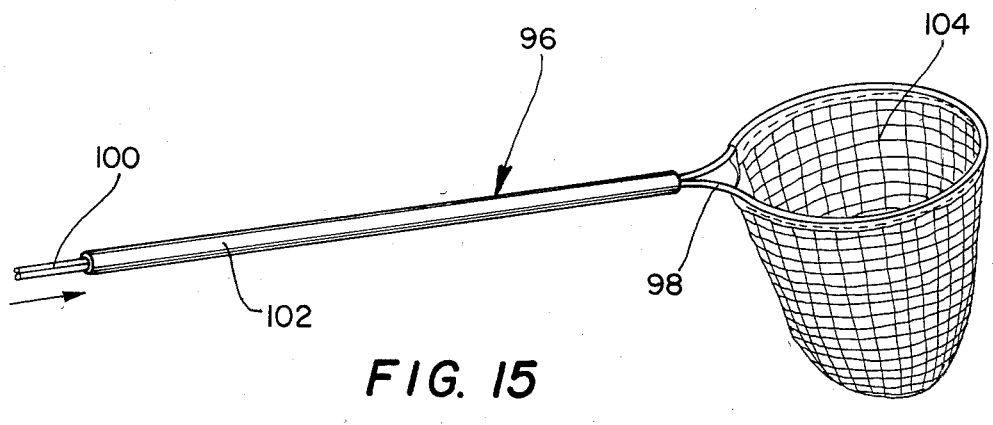
FIG. 15 is a perspective view of a net appliance which is operable in combination with the second embodiment of the ureteroscope of the instant invention.

Referring now to the drawings, a first embodiment of the ureteroscope of the instant invention is illustrated in FIGS. 1 through 4 and generally indicated at 10 in FIG. 1. The ureteroscope 10 comprises a sheath 11 having distal and proximal ends 12 and 13, respectively, a telescope assembly generally indicated at 14, a pair of jaws generally indicated at 16, a handle 18, a ring assembly 20 which is mounted on the sheath 11 in spaced relation to the proximal end 13 and which is operable for manipulating the jaws 16 from the proximal end 13, and first and second irrigation assemblies generally indicated at 22 and 24, respectively. The instrument 10 is operable for effecting surgical procedures within the ureter under direct visual control. Specifically, the instrument 10 is receivable through the urethra and bladder of a patient so that the jaws 16 and the distal end 12 of the sheath 11 are received in the ureter. The telescope assembly 14 is operable adjacent the proximal end 13 of the sheath for direct visualization of the area of the ureter adjacent the distal end 12.

The sheath 11 is preferably constructed of a nontoxic material, such as stainless steel, and comprises an elongated main portion 26 which is dimensioned to be received in a human body so that it extends through the urethra and substantially through the bladder, a tapered portion 28 which extends from the main portion 26, and a reduced terminal portion 30 which extends from the tapered portion 28 and which is dimensioned to be received in the ureter of a patient. The tapered portion 28 is formed to provide a smooth, gradual transition between the main portion 26 and the reduced terminal portion 30 to permit the atraumatic passage of the sheath 11 through the urethra and into the bladder. Preferably, the sheath 11 is constructed so that it has a substantially smooth, continuous circumferential outer surface and preferably the sectional dimension of the main portion 26 is approximately seven to eight millimeters, whereas the sectional dimension of the reduced terminal portion 30 is substantially uniform and approximately three to four millimeters. Extending longitudinally through the sheath 11 is a telescope passage 32, and reduced wire passages 34 also extend longitudinally through the sheath 11 from the distal end 12 to points adjacent the ring assembly 20. A bladder irrigation passage 36 extends longitudinally through the sheath 11 from the first irrigation assembly 24 to a point adjacent the distal end of the main portion 26, and a ureter irrigation passage 38 extends from the second irrigating assembly 24 to the distal end of the sheath 11. The sheath 11 is constructed so that the main portion 26 has sufficient strength and rigidity to permit the use thereof within the urethra and bladder. The terminal portion 30 is constructed in a reduced sectional dimension to permit the insertion thereof in the ureter.

The telescope assembly 14 comprises a conventional endoscopic telescope assembly and includes a base portion 40, a fiberoptic light bundle 42 and an eye piece 44. Also included in the telescope assembly 14 is an elongated lens portion generally indicated at 46 which includes an elongated cylindrical lens 48 having a metallic outer casing 50. The telescope assembly 14 is received in the sheath 11 with the lens portion 46 received in the passage 32, and a tightening knob 52 which extends from the base portion 40 is operable for securing the telescope assembly 14 in the sheath 11 in a conventional manner. The telescope assembly 14 is operable for providing visual communication between the distal end 12 and the proximal end 13 whereby a viewer can observe the area adjacent the distal end 12 by looking through the eye piece 44. The fiberoptic light bundle 42 provides illumination for such viewing.

The jaw assembly 16 comprises a pair of jaw elements 54, a plurality of elbow members 56 pivotally attached to the jaw elements 54, and a plurality of elongated wire elements 58 which extend from the elbow members 56. The jaw elements 54 are formed with slightly arcuate cross section so that they conform substantially to the outer configuration of the sheath 11 as illustrated most clearly in FIG. 4. The jaw elements 54 are hingedly attached to the distal end 12 of the sheath 11 adjacent the outer periphery thereof as at 60 so that they extend with substantially flush to the outer surface of the sheath 11. The jaw elements 54 are preferably curved slightly inwardly, as also illustrated in FIG. 4, so that they are effective for grasping elements such as stones or the like within the ureter. The elbow members 56 are pivotally attached to the jaw elements 54 and extend inwardly and then rearwardly therefrom, respectively; and the wire elements 58 are connected to the elbow members 56 and extend rearwardly therefrom, being slidably received in the passages 34 and extending rearwardly to the ring assembly 20 as illustrated in FIG. 1. The jaw assembly 16 is operable by manipulating the ring assembly 20 to longitudinally advance and retract the wire elements 58 within the passages 54 to thereby move the elbow members 56 to hingedly open and close the jaw elements 54.

The handle 18 is secured to the sheath 11 adjacent the proximal end 13 thereof and is preferably configured similar to a pistol handle, as illustrated in FIG. 1. The handle 18 is preferably positioned to facilitate the manipulation of the ring assembly 20 with the forefinger when the handle element 18 is received in the palm of the hand.

The ring assembly 20 preferably comprises a substantially circular ring element 62 which is attached to a sleeve 64 slidably received on the sheath 11. The wire elements 58 are preferably attached to the sleeve 64 as at 66 whereby the longitudinal movement of the sleeve 64 on the sheath 11 causes the wire elements 58 to be moved within the passages 34 to effect the opening and closing of the jaw elements 54.

The irrigation assemblies 22 and 24 are mounted on the sheath 11 adjacent the proximal end 13 thereof. The first irrigation assembly 22 is mounted so that it communicates with the bladder irrigation passage 36, and the second irrigation assembly 24 is mounted so that it communicates with the ureter irrigation passage 38. The irrigation assemblies 22 and 24 preferably comprise valves of the "stopcock" type having valve bodies 68 and operating levers 70 which are operable to effect the opening and closing of the assemblies 22 and 24. The assemblies 22 and 24 are connectable to various conventional irrigation apparatus to alternately introduce and withdraw various fluids from the bladder and ureter, respectively.

The ureteroscope 10 is operable in the manner illustrated in FIG. 7 for carrying out various surgical procedures within the lower portion of the ureter under direct visual control. Specifically, the sheath is inserted into a patient so that it extends through the urethra 72 and into the bladder 74 of the patient and so that the reduced terminal portion 30 of the sheath 11 extends through the bladder wall 75 and into the ureter 76 of the patient. Since the sheath 11 actually extends slightly into the ureter 76, direct visualization of the area of the ureter 76 adjacent the distal end 12 is possible through the telescope assembly 14. Specifically, by looking through the eye piece 44, a physician can view the inner terminal portion of the ureter 76 adjacent the bladder 74, and various procedures can be carried out within the ureter 76 under direct visual control. In this regard, the jaw assembly 16 can be remotely manipulated with the ring assembly 20 to carry out various procedures, such as the removal of stones or the like from the ureter 76. Further, during these various procedures irrigation of either the bladder and/or the ureter can be effected with the irrigation assemblies 22 and 24 through the irrigation passages 36 and 38, respectively.

The distal end portion of an alternate embodiment of the ureteroscope of the instant invention is illustrated in FIGS. 8 through 10 and is generally indicated at 77. The instrument 77 is substantially the same as the instrument 10 but has jaw elements 78 with ridges 78a thereon closely spaced from the terminal ends thereof for enhancing the use of the jaw elements 78 in dilatng a ureter. Specifically, the terminal portions of the jaw elements 78 are receivable in a ureter 76, and the ridges 78a prevent the ureter 76 from sliding further onto the jaw elements during dilating, as illustrated in FIG. 9. The use of the jaw elements 78 for gripping and removing a stone 79 is illustrated in FIG. 10.

A variety of other embodiments of the ureteroscope of the instant invention are also contemplated for use in carrying out specific surgical procedures. In this regard, the distal end portion of a second embodiment of the ureteroscope of the instant invention is illustrated in FIGS. 5 and 6 and generally indicated at 80. The distal end portion 80 is of slightly arcuately tapered or rounded configuration and comprises the distal end portion of a sheath 81 which includes main, tapered and terminal portions which are preferably dimensioned similar to the corresponding portions of the sheath 11. The sheath 81 is, however, constructed for use in surgical procedures which do not require the jaw assembly 16. Therefore, the ureteroscope of the instant invention as embodied with the sheath 81 does not include a jaw assembly 16 or a ring assembly 20. It does, however, include a telescope assembly 14, a handle 18 and irrigation assemblies 22 and 24. The arcuately tapered or rounded configuration of the distal end portion 80 is particularly adapted for atraumatic entry into the urethra and ureter. The sectional configuration of the distal end portion 80 of the sheath 81 is illustrated in FIG. 6. As will be seen, the sheath 81 includes a longitudinal telescope passage 82, a pair of ureter irrigation passages 84, and an appliance passage 86, all of which extend longitudinally through the sheath 81. The telescope passage 82 is constructed for receiving a telescope assembly 14, in particular the lens portion 46 thereof, and the ureter irrigation passages 84 are constructed for connection to a ureter irrigation assembly 22. A bladder irrigation passage 30 (not shown) is also preferably provided in the sheath 81 and is connectable to a bladder irrigation assembly 24. The appliance passage 86 extends through the sheath 81 to a point adjacent the proximal end thereof and is provided in the sheath 81 for receiving various appliances to conduct various specific surgical procedures within the ureter, as will hereinafter be more fully set forth. In this connection, it will be apparent that the sheath 81 is received in a patient so that the reduced distal end portion 81 is receivable in the ureter of the patient in a manner similar to that illustrated for the sheath 11 in FIG. 7. Once the sheath 81 has been installed in this manner, various appliances are inserted through the appliance passage 86 to carry out various surgical procedures.

The dilating appliance illustrated in FIGS. 11 through 13 and generally indicated at 88 is constructed for use in combination with the sheath 81 and is operable for dilating the terminal portion of the ureter of a patient. The dilating appliance 88 comprises a tubular catheter 90 having a rounded and tapered end portion 92 which provides a closure for the end of the catheter 90, and a dilating balloon 94. The balloon 94 is received on the terminal portion of the catheter 90 so that it is in fluid communication with the interior of the catheter 90 and is expandable by passing fluid through the tubular catheter 90 and into the balloon 94. In this connection, however, the balloon 94 is formed so that when it is inflated it assumes a barbell-like configuration having enlarged end portions and a reduced central portion. It is also preferably calibrated so that there is a known correlation between the amount of fluid fed into the catheter 90 and the cross-sectional dimension of the balloon 94 at various points in the longitudinal extent thereof whereby the inflation of the balloon 94 to the desired extent can be effected. The dilating appliance 88 is operable in combination with the sheath 81 for dilating the terminal portion of the ureter. Specifically, when the ureteroscopoe as embodied with the sheath 81 is inserted into a patient, it is positionable so that the end portion 80 of the sheath 81 is adjacent the ureter where it passes through the bladder wall. The dilating appliance 88 is then passed through the appliance passage 86 and is positioned so that the portion of the ureter where it passes through the bladder wall 75 is adjacent the reduced central portion of the balloon 94. The balloon 94 is then inflated with a fluid to dilate the terminal portion of the ureter. However, since the portion of the ureter where it passes through the bladder wall is adjacent the reduced central portion of the balloon 94, the slippage of the balloon 94 from the ureter is avoided so that the terminal portion of the ureter can be effectively dilated. By providing a calibration between the amount of fluid passed through the catheter 90 and the dimension of the balloon 94 at various points in the longitudinal extent thereof, it is possible to accurately dilate the lower terminal portion of the ureter to the desired degree.

Figure 16:
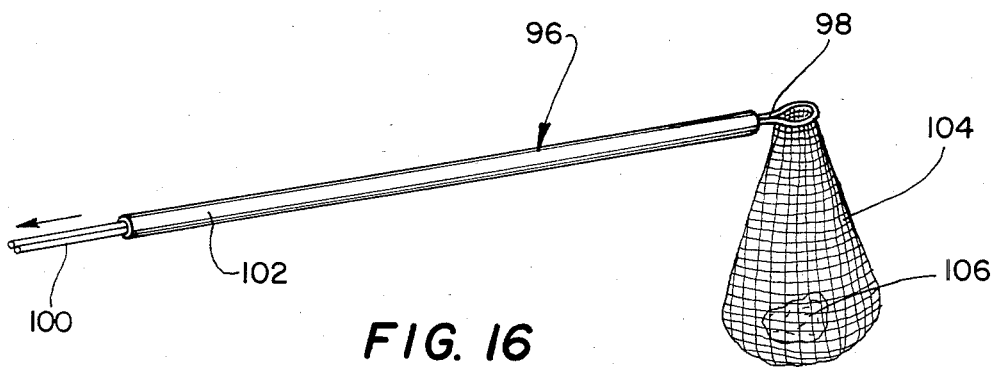
FIG. 16 is a view of the net appliance in the closed position thereof with a stone received therein.

The net appliance illustrated in FIGS. 15 and 16 and generally indicated at 96 is also operable in combination with the ureteroscope of the instant invention as embodied with the sheath 81. The appliance 96 comprises an elongated wire element which is formed to define a wire loop 98 and a pair of coextensive legs 100. The legs 100 are slidably received in an elongated tubular sleeve 102, and the wire loop 98 is contractable to a reduced dimension by sliding the sleeve 102 over the legs 100 so that the portions of the wire element which normally define the loop 98 are positioned within the sleeve 102. A net element 104 is slidably mounted in a purse-like manner on the wire loop 98, and accordingly the net element 104 is closable by contracting the wire loop 98 as illustrated in FIGS. 15 and 16. The net appliance 96 is receivable in the appliance passage 86 of the sheath 81 so that it is operable for retrieving stones and the like from the ureter. In this connection, it is contemplated that in most applications the sheath 81 will be inserted into the patient so that the distal portion 80 thereof is received in the patient's ureter. The net appliance 96 can then be fed through the appliance passage 86 and into the ureter, and the appliance 96 can be manipulated from a point adjacent the proximal end of the sheath 81 to retrieve and capture a stone or the like. This procedure can be carried out under direct visual control with the telescope assembly 14. After the stone or the like, such as the one illustrated in FIG. 16 and indicated at 16, has been retrieved with the net appliance 96, the sheath 81 can be withdrawn from the patient, leaving the net appliance 96 in the patient. Thereafter the net appliance 96 can be withdrawn from the patient to remove the stone or the like with a minimal amount of trauma to the patient. It should be pointed out, however, that although the net appliance 96 is operable in this manner, the use thereof in other surgical procedures for retrieving stones and the like is also also contemplated. Further, the use of the net appliance 96 for retrieving stones or the like from other body cavities is also contemplated.

It is seen, therefore, that the instant invention provides an effective ureteroscopoe which is operative in a variety of embodiments and in combination with a variety of appliances for effecting surgical procedures within the ureter under direct visual control. The dimensions and configurations of both the sheath 11 and the sheath 81 permit their insertion into patients for carrying out surgical procedures within the ureters of the patients, and the telescope assemblies 14 provides direct visual control of the surgical procedures. Accordingly, the instant invention represents a significant advancement as far as patient safety and comfort are concerned and eliminates many of the difficulties heretofore experienced with carrying out operative procedures in the ureter. As a result, the instant invention represents a significant advancement in the medical art which has substantial merit for both commercial and medical reasons.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A surgical instrument for the human body comprising an elongated, substantially straight, substantially rigid sheath of one piece construction having distal and proximal ends and having a longitudinal passage therethrough, said sheath comprising an elongated main portion extending from the proximal end of said sheath which is dimensioned for insertion into a patient so that it extends through the urethra into the bladder of said patient, and an elongated reduced terminal portion of rigid construction and substantially uniform sectional dimension at the distal end of said sheath communicating with said main portion and dimensioned to be received through the bladder wall and a distance into the ureter of said patient, said sheath having a substantially smooth, continuous circumferential outer surface which extends from a point in said main portion to said distal end, said passage extending through said terminal portion to said distal end, and telescope means received in said passage operable from a point adjacent the proximal end of said sheath for providing visual communication with the area adjacent the distal end thereof.

2. In the instrument of claim 1, said sheath having a bladder irrigation passage therein which extends from a point adjacent said proximal end thereof to a point in said main portion adjacent said tapered portion.

3. In the instrument of claim 2, said sheath having a ureter irrigation passage therein which extends from a point adjacent said proximal end thereof to said distal end thereof.

4. In the instrument of claim 1, said sheath having a ureter irrigation passage therein which extends from a point adjacent said proximal end thereof to said distal end thereof.

5. The instrument of claim 1 further comprising hingeable jaw means attached to the distal end of said sheath and means for remotely manipulating said jaw means from a point adjacent the proximal end of said sheath.

6. In the instrument of claim 5, said jaw means comprising a pair of jaw elements which extend from the distal end of said sheath so that the outer surfaces of said jaw elements extend substantially flush with the outer surface of said terminal portion.

7. In the instrument of claim 5, said jaw means comprising a pair of jaw elements which are hingeably attached to said terminal portion so that they extend from said distal end of said sheath, each of said jaw elements having a ridge on the outer surface thereof.

8. In the instrument of claim 7, each of said ridges being adjacent the terminal end of the respective jaw element.

9. In the instrument of claim 1, said sheath having a longitudinal appliance passage therethrough.

10. The instrument of claim 9 further comprising closable net means received in said appliance passage operable from a point adjacent the proximal end of said sheath for retrieving a stone or the like adjacent the distal end thereof.

11. In the instrument of claim 10, said net means comprising a collapsible loop element, a net element received on said loop element, and means for remotely manipulating said loop element from a point adjacent the proximal end of said sheath.

12. In the instrument of claim 10, said net means comprising a tubular sleeve, an elongated wire element formed so that it doubles back on itself to define a loop and first and second coextensive legs of said wire element, said first and second legs being slidably received in said sleeve and manipulatable to alternately expand and contract the dimension of said loop, a net element received on said wire element loop and closable by manipulating said wire element legs to contract said loop, and means for remotely manipulating said legs from a point adjacent the proximal end of said sheath.

13. The instrument of claim 9 further comprising a ureter dilating balloon inflatable to a barbell-like configuration, and means received in said appliance passage operable for positioning said balloon adjacent the distal end of said sheath and for selectively inflating and deflating said balloon.

14. In the instrument of claim 1, the distal end of said sheath being of slightly rounded, tapered configuration.

15. In the instrument of claim 1, the cross-sectional dimension of said terminal portion being approximately half the cross-sectional dimension of said main portion.

16. The instrument of claim 1 further characterized by the presence of a tapered portion on said sheath interconnecting said main and reduced portions.

* * * * *